United States Patent [19]
Ritschel

[11] Patent Number: 5,356,819
[45] Date of Patent: Oct. 18, 1994

[54] METHOD OF DETERMINING CHEMICAL AND/OR PHYSICAL PROPERTIES OF A GASEOUS ATMOSPHERE

[76] Inventor: Manfred Ritschel, Linowskistrasse 11, D-5303 Bornheim 4, Fed. Rep. of Germany

[21] Appl. No.: 946,424
[22] PCT Filed: Feb. 27, 1992
[86] PCT No.: PCT/EP92/00429
 § 371 Date: Nov. 6, 1992
 § 102(e) Date: Nov. 6, 1992
[87] PCT Pub. No.: WO92/15865
 PCT Pub. Date: Sep. 17, 1992

[30] Foreign Application Priority Data
Mar. 7, 1991 [DE] Fed. Rep. of Germany ....... 4107295

[51] Int. Cl.$^5$ .................. G01N 25/18; G01N 31/00
[52] U.S. Cl. .................. 436/147; 436/149; 73/25.01; 73/25.03; 422/82.01; 422/82.02
[58] Field of Search ............ 436/147, 149; 73/25.03, 73/25.01; 422/82.01, 82.02

[56] References Cited
U.S. PATENT DOCUMENTS

| | | | |
|---|---|---|---|
| 2,042,646 | 6/1936 | Willenborg | 436/149 |
| 2,508,572 | 5/1950 | Hulsberg | 73/25 |
| 4,339,949 | 6/1982 | Bahner et al. | 73/204 |
| 4,735,082 | 4/1988 | Kolloff | 73/27 R |
| 4,741,198 | 5/1988 | Farren et al. | 73/23.1 |
| 4,813,267 | 3/1989 | Norem et al. | 73/23.1 |
| 4,850,714 | 7/1989 | Wiegleb | 374/44 |

FOREIGN PATENT DOCUMENTS

| | | |
|---|---|---|
| 0431394A2 | 6/1991 | European Pat. Off. |
| 2039515 | 2/1972 | Fed. Rep. of Germany |
| 3005121A1 | 8/1981 | Fed. Rep. of Germany |

OTHER PUBLICATIONS

*6.4 Thermokatalytische Sensoren,* "6.4.1 Mehodische Grundlagen und Bauformen".

Primary Examiner—Nina Bhat
Attorney, Agent, or Firm—Spencer, Frank & Schneider

[57] ABSTRACT

A method of determining at least one of chemical properties, physical properties and physical states of a gas atmosphere, including the steps of (a) bringing the gas atmosphere into contact with a heatable surface while heating up the heatable surface from a starting temperature to a predetermined higher temperature by the addition of energy thereto over a period of heating time; (b) discontinuing the addition of energy when the predetermined higher temperature is reached; and (c) evaluating heat discharged by the heatable surface under the influence of the gas atmosphere as a function of time to generate a measuring signal. Heating up of the heatable surface by the addition of energy is preferably effected over a period of heating time which is a limited period of heating time, and occurs cyclically at successive intervals in time as a heating cycle.

13 Claims, 16 Drawing Sheets

METHOD OF DETERMINING CHEMICAL AND/OR PHYSICAL PROPERTIES OF A GASEOUS ATMOSPHERE

BACKGROUND OF THE INVENTION

1. Field of the Invention

The invention relates to a method of determining chemical and/or physical properties of a gas atmosphere, wherein the gas atmosphere to be examined is brought into contact with a heatable surface and the resulting changes in the temperature level are converted into an electrical signal.

2. Description of the Related Art

The analysis of the chemical properties of a gas atmosphere essentially involves the question of what kind of gas is in the gas atmosphere or, for gas mixtures, whether one or several certain gases are present in the gas atmosphere. Such an analysis is made, for example, in coal mining to check for the presence of pit gases, particularly methane gas. Such analyses of the composition of gas atmospheres and the checking for the presence of certain types of gas in a gas atmosphere constitute the major field of use for such methods. The analysis of the physical properties of a gas atmosphere in the sense of the present invention relates primarily to the determination of conductivity, convection, heat tone and flow velocity of the gas atmosphere to be tested. The term gas atmosphere includes a pure gas as well as gas mixtures.

In the past, such analyses of a gas atmosphere have been effected in that a wire heated by an electrical current and having thermocatalytic properties was placed into a chamber containing the gas atmosphere to be analyzed, preferably with the gas atmosphere to be analyzed flowing through the chamber. The heating wire was connected with appropriately adapted resistors in a Wheatstone bridge configuration. With the aid of such an arrangement it is possible, for example, to measure the quantity of heat carried off by a gas flowing by and, with the appropriate calibration, information can be obtained regarding the flow velocity (see Friedrich Oehme, "Chemische Sensoren" [Chemical Sensors], 1991, FIGS. 6–12).

The determination of the presence of certain types of gas in the gas atmosphere to be examined is possible with the prior art methods only if the gas atmosphere is to be examined for the presence of reactive gases, for example the presence of methane gas or the like. By setting a certain thermocatalytic temperature at the heating wire, a reactive gas will react with the remaining gases contained in the gas atmosphere; for example, the reaction of methane with the oxygen from the air results in an increase in temperature which then "detunes" the Wheatstone bridge so that a signal can be initiated there.

In addition to the above mentioned, very limited possible uses for the prior art methods, another drawback is the use of the Wheatstone bridge circuit as a measuring system. Such a bridge circuit is in itself temperature dependent to a considerable degree since the resistors connected to the heating wire by themselves are also subject to temperature influences so that the bridge circuit is detuned then as well and error measurements result if, due to extraneous temperature influences, the resistors inserted in the circuit are subjected to temperature fluctuations and thus change the zero balance of the circuit. Another drawback of the prior art manner of proceeding is that a considerable amount of current is required to constantly heat the heating wire connected with the gas atmosphere so that mobile measuring instruments require large-capacity batteries which nevertheless permit only limited use times before they must be recharged again. Another drawback of the prior art method is that the system operates with relatively slow response times. Since overheating of the heating wire may also occur which changes the behavior of the wire, the instrument must be recalibrated after every response. Such a measuring device is unstable and not suited for permanent use, for example for monitoring purposes.

It is now an object of the invention to provide a method with which practically all types of gas can be detected in a gas atmosphere and changes in the composition of the gas atmosphere can be analyzed, with current consumption as well as response time being reduced.

SUMMARY OF THE INVENTION

This is accomplished according to the invention in that the heatable surface is heated by the supply of energy; the heat output of the surface under the influence of the gas atmosphere to be analyzed is recorded and the temperature curve resulting from the influencing is evaluated for the generation of a measurement signal. This method offers a number of advantages: heating of the surface can be effected directly by means of a wire through which a current flows or indirectly by means of temperature radiation, for example, by means of a laser beam or other heat generating types of radiation (microwaves, induction). Another advantage of the method according to the invention is that it is possible to detect the presence of reactive as well as non-reactive gases in gas mixtures already at temperatures which lie below the reaction temperature since these relationships are determined exclusively by the conductivity and heat absorption capability of the gases or gas mixture. The consequence is the advantage, particularly for an analysis of reactive gases, that with the appropriate configuration the method according to the invention can easily be configured as an explosion protected system since, depending on the configuration of the process, it is no longer required to have a chemical reaction of any kind in order to determine the gas. The particular advantage of the method according to the invention is that, for example, in a wire through which current flows, it is not the change in the current and/or voltage caused by the emission of heat that is detected for the generation of a measurement signal but the change in temperature of the heated surface. Thus a short response time results since temperature changes occur in the fourth power. If a heating wire is employed it is thus also possible to prevent overheating, that is, heating to above a permissible temperature, since together with the actuation of a measurement signal the energy supply can also be reduced or switched off altogether. This is of particular advantage for simple constant-monitoring tasks.

One advantageous feature of the invention provides that the heatable surface is heated by the supply of energy at successive time intervals over a predetermined period of time (heating cycle). Thus energy is supplied, on the one hand, at successive time intervals and, on the other hand, also only over a certain period of time. This reduces current consumption. Another advantage of the method is that, as described above, the analysis of the chemical and/or physical properties is not based on a temperature measurement but is effected by way of a time measurement. In this connection, advantage is taken of the fact that the modern electronic art has available digitally operating time measuring components, that is, basically counters, which can be employed as passive as well as active elements. An active element in the sense of the present invention is such a component in which the time intervals that must be maintained between the individual heating cycles are predetermined as well as the length of the respective heating cycle itself. Passive arrangements in the sense of the invention are those in which, inversely, it is determined how much time has expired until a certain temperature is reached and the determined time is then evaluated for the generation of a measurement signal. Based on the relationship between measured time and determined temperature curve, it is thus possible to detect different conditions in the gas atmosphere to be examined since different gas atmospheres also result in different relationships between the temperature curve and the heating cycle. These relationships can be calibrated so that a reliable measurement is possible.

One feature of the invention provides that, in connection with a heatable surface, the characteristic of the gas atmosphere which influences the emission of heat can be determined by measuring the intensity of the heat radiation emanating from the surface. This manner of proceeding takes advantage of the fact that different gases have different thermal conductivities. Thus it is possible to determine in a simple manner changes in a gas atmosphere that is to be monitored constantly and to employ the method, for example, for gas warning devices that are also provided with a heating wire through which a current flows constantly. Thus it is further possible to detect [not only] pure gases but also gas mixtures, that is, to analyze gases since, with a given heating rate, that is with a given supply of energy per unit time, the conductivity of each gas gives it its own characteristic thermal radiation. The intensity of the radiation determined during the time unit, that is, at the end of each heating cycle, is a measure for the type of the measured gas and for the composition of the respectively measured gas atmosphere if the latter is present in a mixture as a binary or tertiary system as this is the case, for example, for a mixture of air and another gas. The determination of the radiation intensity can here be made with the most varied means, preferably those that generate electrical signals, for example, photoelements, photoresistors, thermoelements or other elements that are able to detect infrared radiation, photomultipliers, pyrosensors. The individual sensor elements may be active elements, that is, put out a voltage themselves on the basis of the thermal radiation and thus "generate" a current, as well as inactive elements, that is, they may be connected to an external current supply. In that case, the change in the voltage and/or flow of the current is determined as this is the case in connection with photoresistors.

Another feature of the method provides that the properties of the gas atmosphere are analyzed in that the time is measured during which, starting with the beginning of a heating cycle, the thermal radiation reaches a predetermined intensity threshold. This feature constitutes a modification of the above method. Again, with a predetermined heating rate, the thermal radiation is detected as a function of the interaction of the gas atmosphere with the heated surface. However, it is not the intensity of the thermal radiation that is measured after a predetermined period of time but an intensity threshold is given and it is determined after which time, at the predetermined heating rate, the intensity threshold is exceeded and thus a corresponding signal is initiated. For gases having a high conductivity, this intensity threshold is exceeded after a longer period of time because of the intense heat output of the surface and for gases having a poor conductivity, the intensity threshold is exceeded after a shorter time since the surface puts out little heat. For gas mixtures composed of gases having a low conductivity as well as gases having a high conductivity, the moment at which the intensity threshold is exceeded lies, corresponding to the mixing ratio, between the two corner values which can be determined by way of tables set up from calibration measurements.

As a further feature of the method according to the invention it is provided that the heat output under the influence of the gas atmosphere is analyzed, for an electrically heatable surface, by measuring the electrical current required, at a given voltage, to heat the surface during the respective time period (heating cycle). While for the detection of the radiation intensity, an appropriate sensor element must be provided as an additional element, this manner of proceeding detects the heat output in relation to the heating time. This may again be effected in that either the maximum current intensity realized during a predetermined time period is measured or, again with the predetermined current intensity (current threshold), the time is measured which is required at the given voltage to reach this threshold value. The maximum current intensity during a predetermined heating period as well as the measured time until a predetermined current threshold is reached are a measure for the gas or gas mixture presently in contact with the heatable surface. In this manner of proceeding, the heatable surface itself is preferably electrically conductive, for example in the form of a semiconductor or a metal conductor so that the application of a voltage heats the surface directly with the heat from the current generated thereby. If such a directly heatable surface is in a predetermined but moving gas atmosphere, for example, in a flow channel instead of in a quiescent gas atmosphere, the maximum current intensity or time until the predetermined current threshold is reached during the respective heating cycle is a measure for the flow velocity of the gas in the flow channel.

The above described method employing a directly heated surface and a measurement of the heating current during the heating period, be it by giving the time and measuring the current, be it by giving a current threshold and measuring the time, can also be employed with advantage for monitoring a gas atmosphere with respect to reactive gases. Here again, the heatable surface is set to the ignition temperature of the gases to be detected as the additional components in the existing gas atmosphere. If a corresponding reactive gas is present in a corresponding reactionable quantity percentage with respect to the existing gas atmosphere, then an exothermal gas reaction leads to an increase in the temperature of the heatable surface and an endothermal gas reaction leads to a reduction of the surface temperature independent of the current supply so that the resulting deviation in the relationship between current intensity and time can be evaluated as a measurement signal.

A feature of the method further provides that, during the predetermined time period, the heatable surface is heated in each case starting at a minimum temperature value. Thus it is possible, particularly for an analysis of reactive gases, to keep the heatable surface at a minimum temperature and, starting in each case from this minimum temperature, to periodically raise the temperature to the required reaction temperature. Thus it is possible almost without delay to obtain an indication that the presence of a reactive gas mixture has initiated a reaction.

As a feature of the method according to the invention it is possible to fix the time periods for the supply of electrical heating energy (heating cycle) and the time sequence of the successive heating cycles. Such a setting is permissible, for example, if due to conditions the type of gas to be detected is expected to flow in only slowly and additionally, dangers are expected only if it is present in greater percentages.

As another feature of the method according to the invention it is provided that the beginning of a heating cycle is determined by a set lower temperature threshold and the end of a heating cycle by a set upper temperature threshold and the time sequence of the heating cycles (frequency) serves as a measurement signal for an analysis of the gas atmosphere. This feature of the method has the advantage that changes are detected practically automatically, with even slight changes directly causing a change in the frequency of the heating cycles. While the above-described procedures require a measurement of the time (or the counting of pulses per unit time) and the measurement of a current, that is, the picking up of two measurement values, with both measurement values then having to be related to one another, the last-mentioned feature of the method has the advantage that a lower threshold and an upper threshold for the heating current to be employed or a lower and an upper intensity threshold for the heat radiation emanating from the surface are set, but that the measurement itself is purely a measurement of time or pulses. Thus, this method can be employed, for example, to monitor existing gas atmospheres in which the entrance of easily reacting gases, particularly gases that react already in small quantities with the existing gas atmosphere, for example, the air in the room, is to be detected. The presence of the reactive gas is indicated directly by a change in the frequency of the heating cycles since the upper temperature threshold is reached more quickly, the current supply is switched off and, once the system has cooled to the range of the ignition temperature, the heating current is switched on again to thus initiate a renewed ignition whereupon the upper temperature threshold is again reached very quickly.

A number of further possible technical uses result for the method according to the invention. Thus, in addition to the mentioned determination of the presence of certain gases, it is also possible, for example, to make analyses of the moisture content of gases or, by way of cracking and analyzing the cracking products, to make gaseous compounds detectable at all. In addition to determining chemical properties, this method can also be employed to perform pressure measurements in a vacuum and measurements of gas streams. With the appropriate configuration of the heatable surface, it is possible to utilize, in addition to thermocatalytic processes, also sorption and adsorption processes at an appropriately configured surface for corresponding applications. In all cases, the method according to the invention, particularly in its respective embodiments, offers further possible uses.

BRIEF DESCRIPTION OF THE DRAWINGS

The method according to the invention will now be described in greater detail for embodiments thereof with reference to schematic drawings and diagrams in which.

DESCRIPTION OF THE PREFERRED EMBODIMENTS

Figure 1:
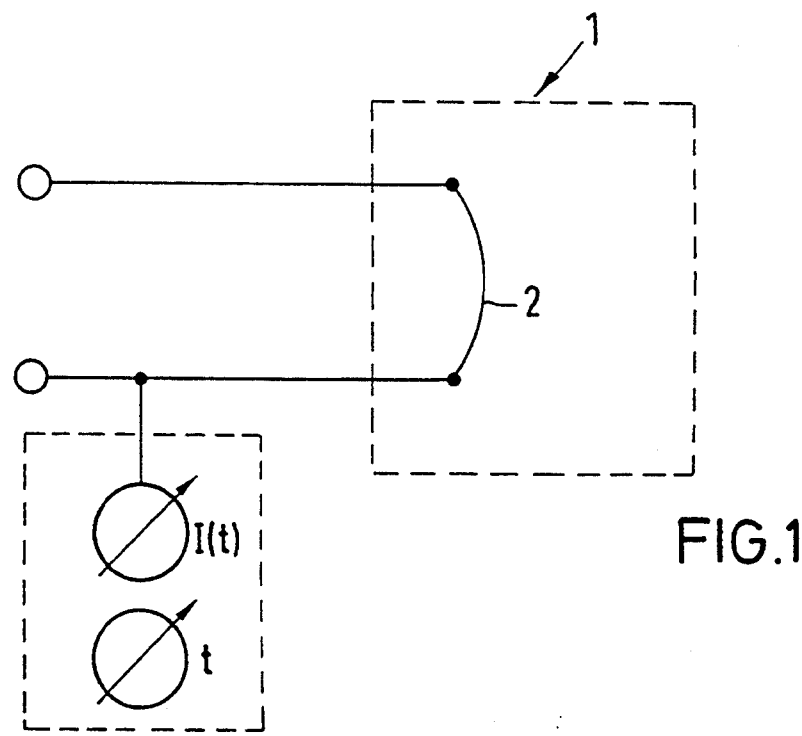
FIG. 1 is a basic sketch of a first embodiment of the method.

FIG. 1 is a schematic illustration of the measuring principle. A directly electrically heatable surface 2 in the form of a heating wire is disposed within a measuring cell 1 containing a measuring gas A or through which a measuring gas A flows. By way of appropriate leads, this heating wire is connected to a voltage source that is not shown in detail here. The current intensity I required to heat the surface is measured, as shown symbolically, as a function of time, with the time measurement being effected up to or between existing thresholds for the heating current depending on the particular case of use during heating or cooling of the surface.

Figure 2:
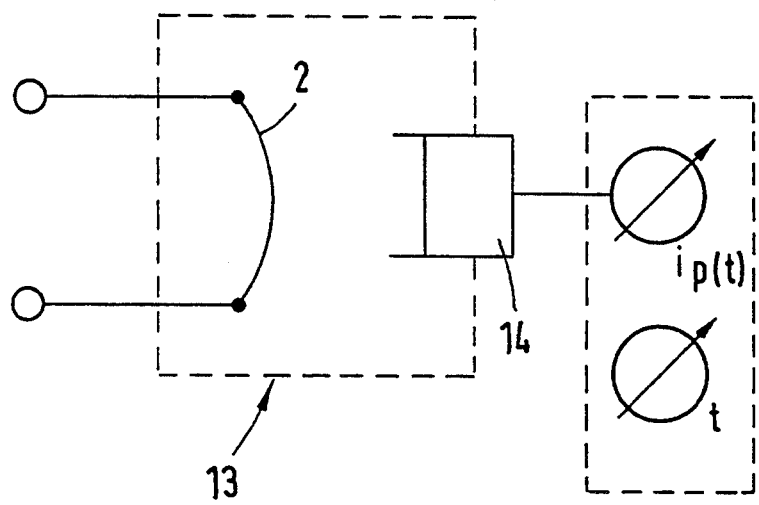
FIG. 2 is a basic sketch of a second embodiment of the method.

FIG. 2 depicts a modification of the method of FIG. 1. Here an electrically heatable surface 2 is again disposed in a measuring cell 13 containing a measuring gas A. While in the principle shown in FIG. 1 the heat dissipated by surface 2 as a result of the influence of the gas atmosphere to be analyzed was picked up directly by way of a change in the heating current relative to the time, the measuring principle shown in FIG. 2 measures the emission of an electromagnetic radiation during heating or cooling of surface 2. For this purpose, a radiation sensor 14 is provided by means of which, as shown schematically, the change in the electromagnetic radiation $i_p$ can again be detected as a function of time. Here again, the time is measured until a predetermined threshold of the emission of electromagnetic radiation is reached during heating or cooling of the surface or until the emitted value reaches a predetermined lower and upper threshold. In a modification, this system may also be employed with a constant energy supply if, for example, for gas warning devices set up for a certain gas, the change in radiation intensity indicative of a warning case is detected by the radiation sensor and initiates a measurement or alarm signal. The different measuring arrangements shown schematically in FIGS. 1 and 2 will now be described individually in greater detail with reference to the block circuit diagrams of FIG. 3 and FIG. 5.

Figure 3:
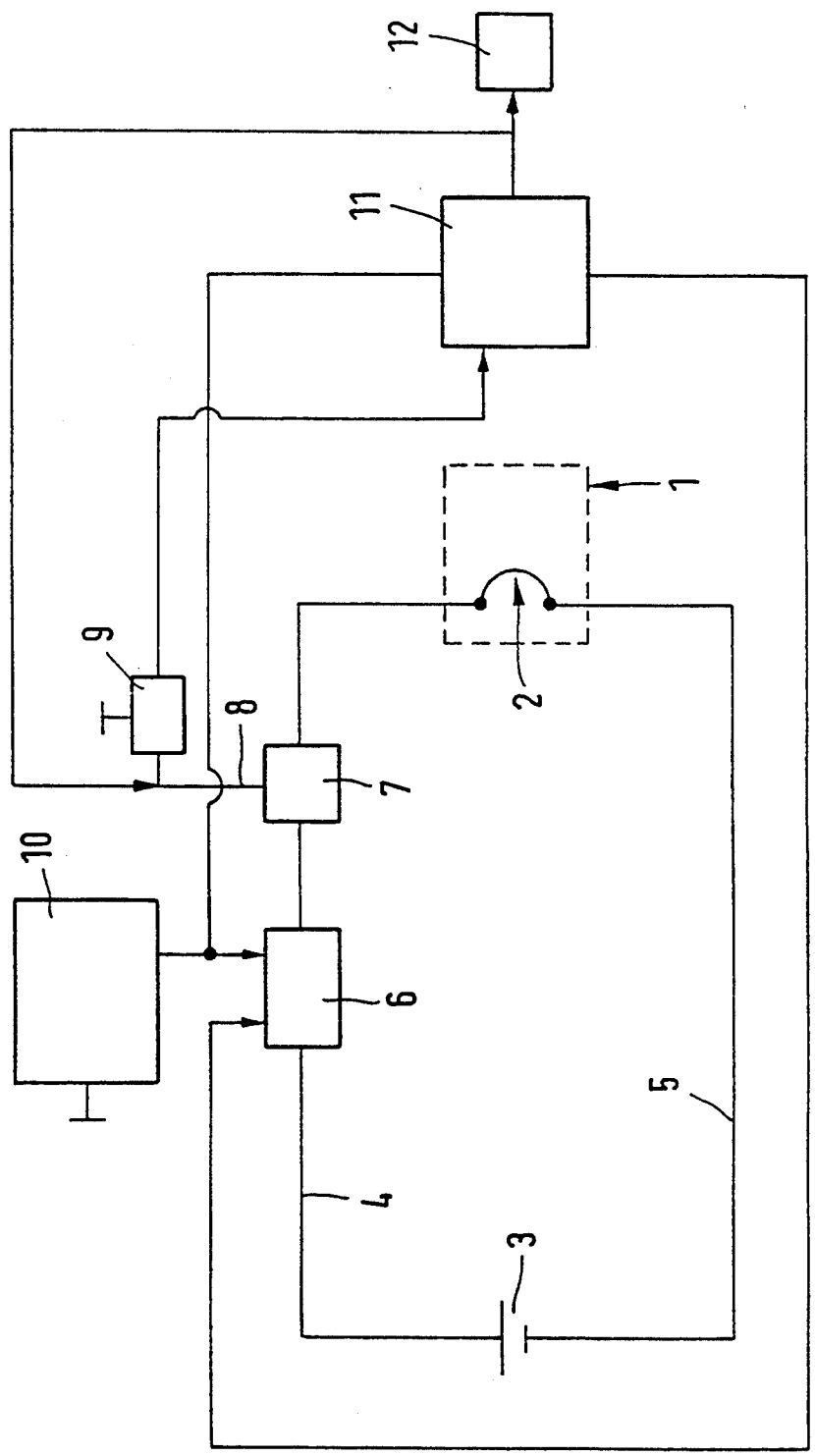
FIG. 3 is a block circuit diagram of the first embodiment for a device according to FIG. 1 for implementing the method.

FIG. 3 depicts, in the form of a block circuit diagram, a device according to FIG. 1 and is essentially composed of a measuring cell i having at least one opening for the entrance and exit of the gas atmosphere to be measured. Particularly for use for the detection of reactive gases, measuring cell 1 is provided with a large number of small passage openings instead of large passage openings in the cell walls. The measuring cell may here, for example, be a hollow body made of a porous sintered material.

The electrically heatable surface 2 which preferably is configured to be directly electrically heatable and may have, for example, the shape of a heating wire is disposed in measuring cell 1. The material to be employed for the heatable surface depends in each case on the intended use and may be produced, for example, from a catalytically active material. Depending on the application, the surface may also be chemically-physically activated for sorption interaction of the gas with the surface. Through lines 4 and 5, the heatable surface is supplied with electrical energy from a current source 3, for example in the form of a rechargeable battery. A switching device 6 with which the current supply can be turned on and off again is disposed in line 4. By way of a measuring device 7 in line 4, the current intensity required in each case to heat surface 2 can be measured, with measuring device 7 being equipped with a signal output 8 in which a threshold setting member 9 is disposed that makes it possible for a signal to be put out only if a certain predetermined current intensity threshold is exceeded.

Switching device 6 is connected with a clock 10 which switches the current supply on at predetermined time intervals by way of switching device 6 in order to heat surface 2.

Clock 10 as well as the measuring device for detecting the current intensity and its threshold setting member 9 are connected to a time measuring device 11, for example in the form of a pulse counter, which is provided with a measurement evaluation unit 12 to display the measuring result. The time measurement thus covers, within the turn-on interval, the pulses emitted at a constant frequency by clock 10. This measurement evaluation unit 12 may be configured as a display device and/or an acoustic and/or optical signalling device and/or may be part of a regulating or control circuit with which safety gates are closed and fans are turned on or the like if, for example, a gas alarm has been initiated.

The method according to the invention will now be described in greater detail and with reference to diagrams for different uses of a device according to FIG. 3.

Figure 4:
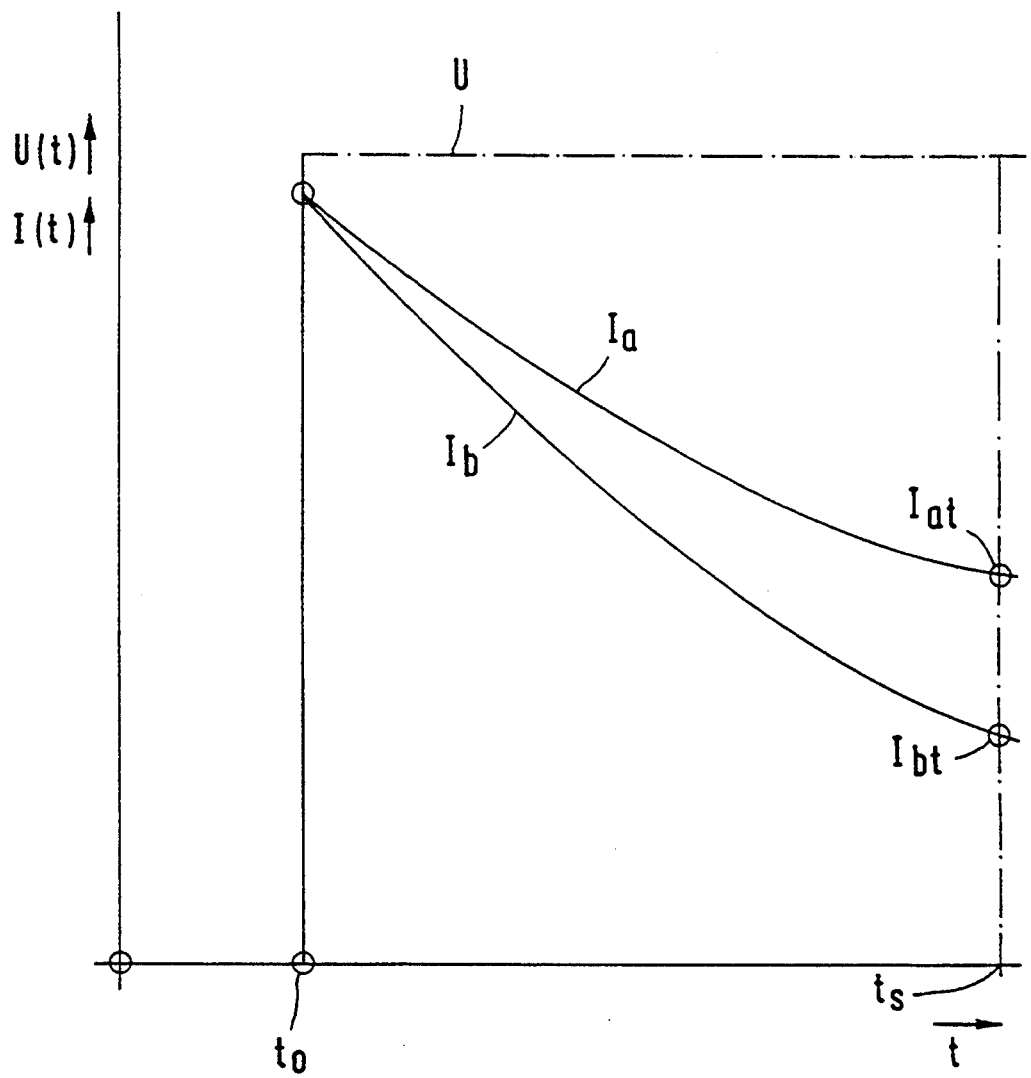
FIG. 4 is a diagram explaining the manner of operating of the device of FIG. 3 in a first manner of proceeding.

If measuring cell 1 contains a gas atmosphere to be tested, clock 10 connects, with the aid of switching device 6, the heatable surface, which is configured, for example, in the form of a heating wire, to the battery voltage. After a time determined by time measuring device 11, the switching device is actuated again and the current supply is switched off. For purposes of monitoring, this process is then successively repeated again and again at certain time intervals. FIG. 4 depicts the curve of voltage U over time t schematically in the form of a rectangular curve for such a heating cycle. If the heatable surface 2 is a heating wire made of an electrically conductive material whose electrical resistance as a function of temperature is known, for example, a material whose resistance rises in the here applicable temperature ranges between, for example, 20° C. and 700° C., then the curve for the current intensity I as represented by curve $I_a$ results in measuring cell 1 if a certain gas atmosphere is present. After the end of a heating cycle predetermined by the clock at time $t_s$, the voltage $I_{at}$ is picked up as a measurement value. If a predetermined "normal atmosphere" is involved, for example air, no signal is initiated.

However, as soon as a further gas, for example a reactive gas such as methane or the like, is additionally present in the existing normal atmosphere, a reaction is initiated under the influence of the temperature of the surface between the methane and the oxygen from the air, resulting in a further rise in the temperature in the measuring cell. This further temperature rise causes the current consumption to be reduced due to the increased electrical resistance of the heating wire embodying surface 2 during the heating cycle, that is, during the interval $t_0$–$t_s$ so that the schematic curve $I_p$ shown in FIG. 4 results. At the end of the heating cycle $t_0$–$t_s$ the much lower current intensity $I_{bt}$ is then detected as the measurement signal. By appropriately presetting a threshold value for current measuring device 7 it is then possible to emit a corresponding switching signal for an alarm, etc., by way of measurement evaluation unit 12.

Figure 5:
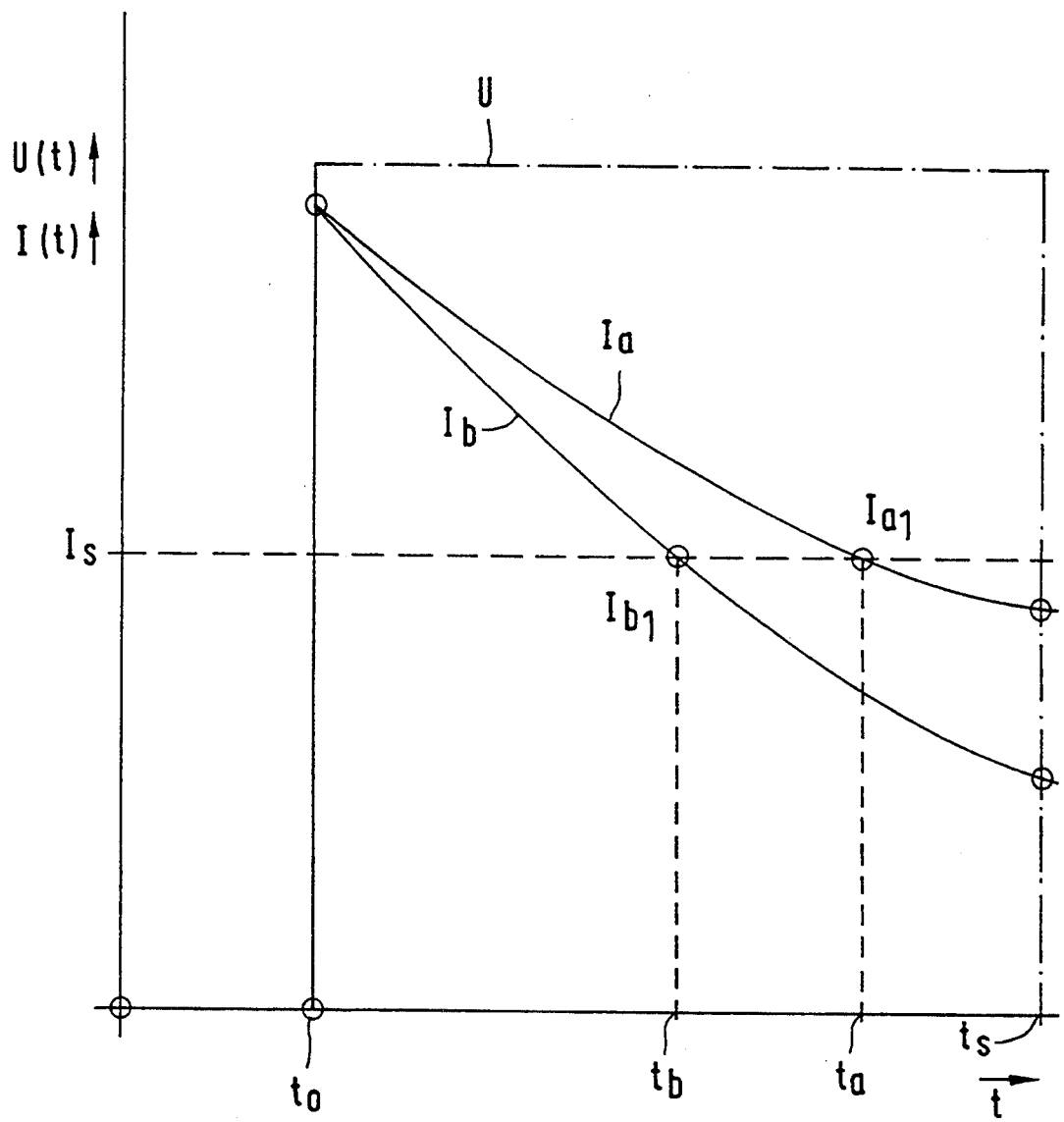
FIG. 5 is a diagram explaining the manner of operating of the device of FIG. 3 in a second manner of proceeding.

The above described manner of proceeding may then be modified in such a way that, as shown in FIG. 5, a threshold value $I_s$ for the current intensity is set for the curve of the current intensity over time. The circuit according to FIG. 3 is now laid out in such a way that the moment in time is measured at which the heating current reaches threshold value $I_{a1}$. The time period $t_0$–$t_a$ is then the "measure" for the presence of the predetermined "normal atmosphere". If now, corresponding to the above-mentioned case of use, methane is contained in the gas atmosphere to be measured in addition to the air forming the normal atmosphere, the reaction of the methane gas with the oxygen from the air leads to a noticeable decrease in current consumption so that the set threshold value $I_s$ is reached already at a much earlier point in time $t_b$ so that thus the much shorter time period $t_0-t_b$ is a measure for an interference with the normal atmosphere by the existing reactive gas and in a dangerous concentration so that here again, as mentioned above, the corresponding switching pulses are put out by way of measurement evaluation unit 12.

The two above examples indicate that the method according to the invention operates no longer solely by way of the current consumption of the heating surface in a manner proportional to the temperature but here additionally includes a time measurement. By appropriately setting the relationship between current and time and by appropriately setting the threshold values for time or current, different measuring ranges can then be set with one and the same measuring device. While in the operating mode described in connection with FIG. 4, the signal is still initiated by a current measurement, that is, the clock merely determines the duration of the individual heating cycle and the time interval between successive heating cycles, in the mode of operation described in connection with FIG. 5 the measurement is effected exclusively by way of a time measurement. Depending on the type of intended use of such a device, the current intensity set as the threshold value can be fixed so that no complicated current measuring devices need be provided. The description of the operating mode further indicates that the measuring method is very sensitive and leads to a signal initiation with only a slight time delay. After prior calibration it is possible to analyze gases or gas mixtures by way of a current measurement and the current value $I_t$ or by way of a time measurement and a set current threshold over the respective time period $t_0-t_x$ during which the set threshold is not reached.

The schematic curves shown in FIGS. 4 and 5 for the course of the current intensity over time which are representative of the temperature conditions at the electrically heated surface 2, also demonstrate the possible use of the method for measuring the current velocity of a gas stream. In this case of use, measuring cell 1 is no longer a closed chamber but part of a flow channel into which the heatable surface 2 projects, for example in the form of a heating wire, a coil or the like. Since a flowing gas atmosphere generally is a gas atmosphere that has a constant composition, information about the flow velocity of the gas in the flow channel can be obtained with this measuring method by way of the quantity of heat picked up from the surface by the flowing gas per unit time and thus the resulting temperature drop within the heating cycle. The advantage is here that the flow in the channel is hardly impaired by a thin glow wire so that the glow wire may be disposed in the undisturbed core region of the flow. In this connection, it must further be considered that it is also possible to vary the respectively realizable maximum temperature at the heatable surface by way of the set heating voltage. For example, it is possible to operate in a temperature range below the ignition temperature even in the presence of reactive gases since the change in the ability of the gas atmosphere to absorb heat when its composition differs from the basic "normal atmosphere" also becomes noticeable by a change in the curve of the heating current.

Figure 6:
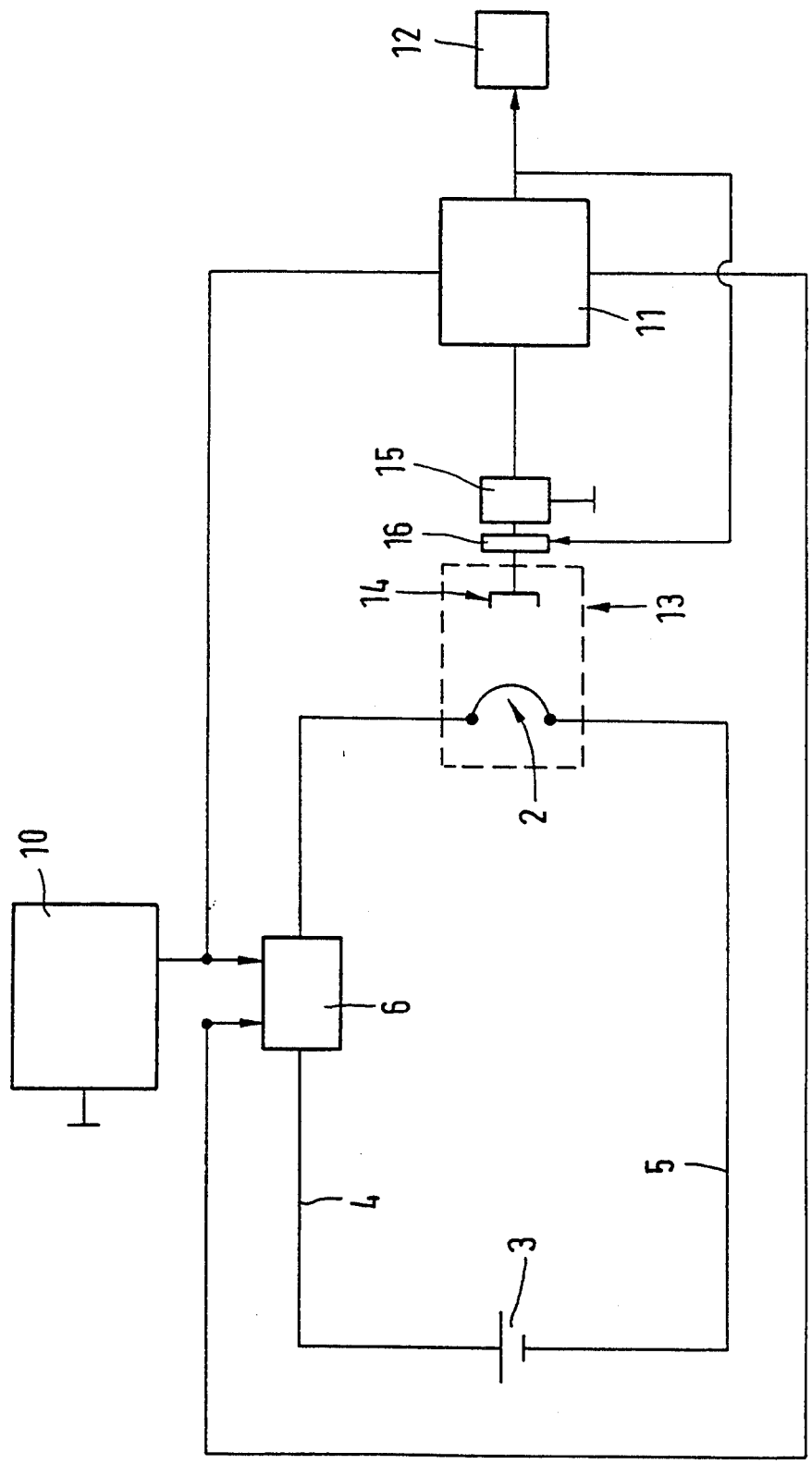
FIG. 6 is a block circuit diagram of the second embodiment of a device according to FIG. 2 for implementing the method.

FIG. 6 depicts a device according to FIG. 2 as a circuit arrangement in the form of a block circuit diagram. In this arrangement, a measuring cell 13 is provided in which a surface 2 is disposed that is heated directly or indirectly, for example electrically. This surface 2 has an associated radiation sensor 14 whose detection surface is oriented toward surface 2. Radiation sensor 14 may be configured as a photoresistor, photodiode, photoelement and also as an infrared radiation measuring device, as a pyroelectric sensor or also as a bolometer. The signal output ip of radiation sensor 14 is connected to an adjustment member 15 with which different measuring signal thresholds can be set. The signal output of adjustment member 15 in turn is connected to a time measuring device 11 of the type already discussed above which in turn is connected with measurement evaluation unit 12.

The heatable surface 2 in turn is connected by way of leads 4 and 5 to a current supply 3, with a switching device 6 again being disposed in lead 4 and being connected with clock 10 in the same function as described already in connection with FIG. 3. Time measurement unit 11 is connected with clock 10 by way of a start switch 16 so that the start of the time measurement can be switched on in each case.

Figure 7:
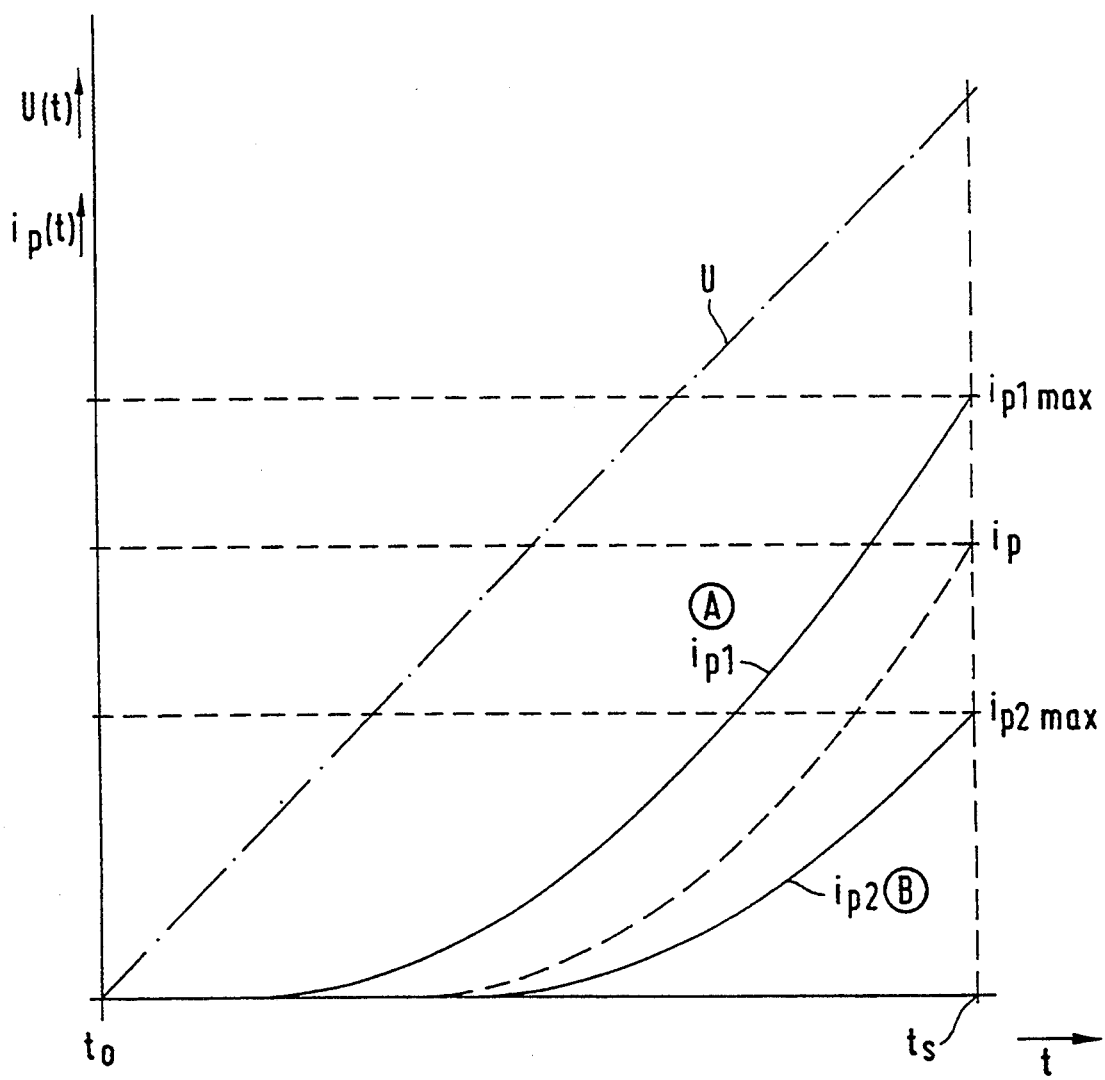
FIG. 7 is a diagram explaining a first operating mode of the device of FIG. 6.

In this measuring device, switching device 6 is configured in such a way that the heating device, if it is an electrically directly heated wire, is not fully connected at the beginning of the turn-on moment but gradually increases over time up to a maximum value. The diagram of FIG. 7 here depicts as an example a linear voltage rise U. Once the set time threshold $t_s$ is reached, the set heating cycle is completed and the voltage is disconnected. This process is then repeated at set intervals.

The radiation intensity passed through the gas atmosphere contained in measuring cell 2 is then detected by way of radiation sensor 14. For a gas A, this results in a curve of intensity $i_{p1}$. For a gas B having a greater conductivity than gas A, the curve for the detected radiation intensity is $i_{p2}$. The maximum intensity value $i_{p1\ max}$ and $i_{p2\ max}$, respectively, determined in each case at time $t_s$, after appropriate calibration, permits an indication of the presence of a certain gas. If one assumes that the illustrated curves $i_{p1}$ and $i_{p2}$ each correspond to the curve of a pure gas, mixtures of gas A and gas B can also be detected since then the curve of the radiation intensity over time results according to the mixing ratio between gas A and gas B between $i_{p1}$ and $i_{p2}$. Instead of a pure gas, curve $i_{p1}$ may, for example, also be set by a gas mixture, for example air, so that then the presence of a further gas in the air brings about a corresponding shift of the intensity curve.

Figure 8:
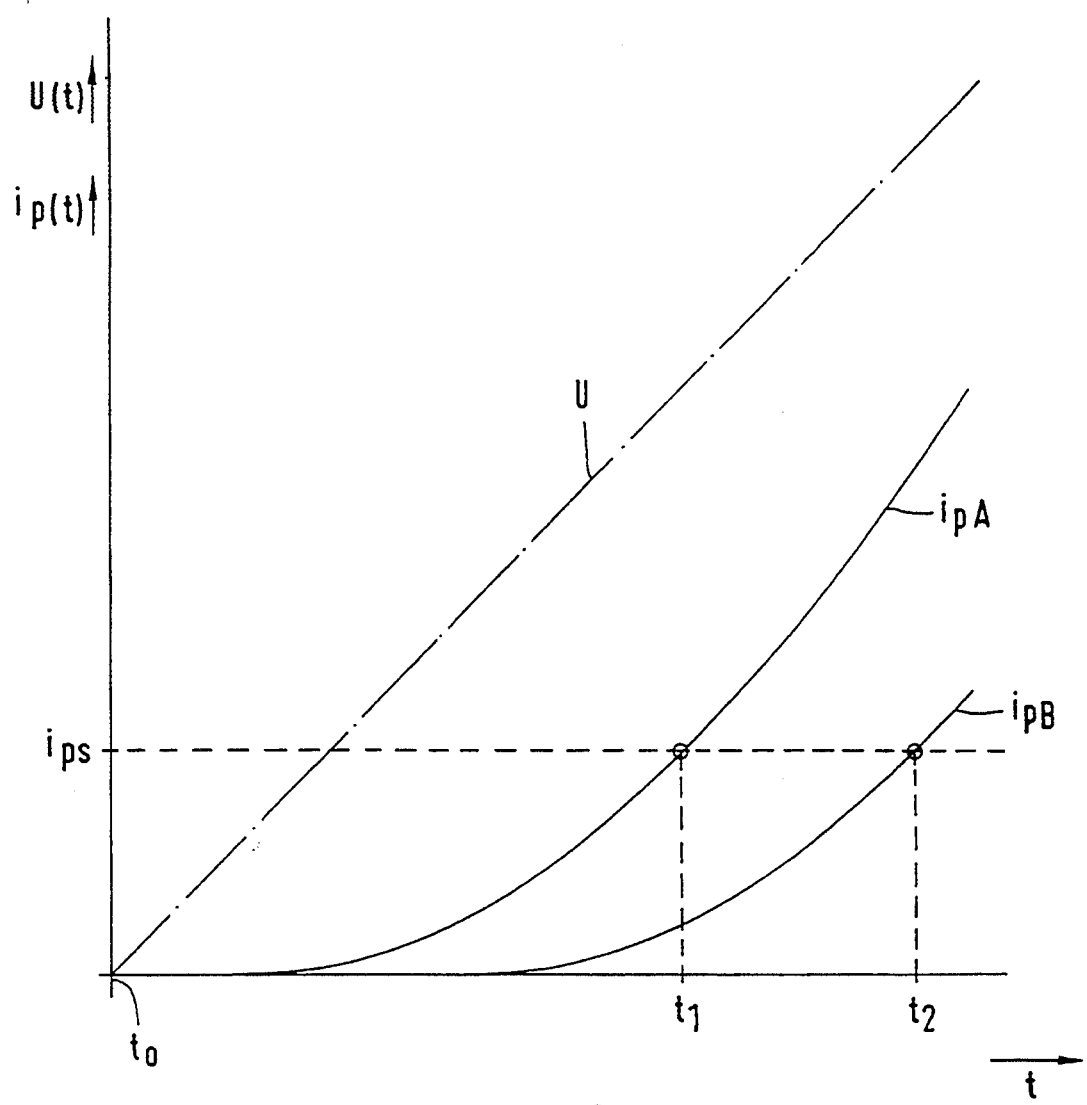
FIG. 8 is a diagram explaining a second operating mode of the device of FIG. 6.

In this manner of proceeding as well, the measurement can again be performed as a pure time measurement as indicated in FIG. 8. In this manner of proceeding, the system again operates with a set rise in the heating voltage. An intensity threshold is set by way of adjustment member 15 in radiation sensor 14 so that a signal is initiated only if the set radiation intensity threshold is exceeded. As indicated in FIG. 8, the intensity threshold is exceeded earlier, that is, at time $t_1$, by a gas having a lower conductivity, while a gas having a higher conductivity exceeds the threshold only at a later time $t_2$.

The operating modes described above for two different measuring devices indicate that with the present method the change over time of radiation emission and/or thermal conductivity of the surface during heating or cooling, respectively, is always detected. Since the "time" factor is included in the measuring method, a dynamic measuring method results which permits the determination of conductivity, composition or velocity of the gas or a gas atmosphere with great sensitivity, selectivity and a short response time. Since in the measuring method employing a measuring device according to FIG. 6, the physical relationships in a chamber are measured, it is also possible, in addition to the above-discussed measurement of composition and conductivity, to also determine a subatmospheric pressure of gases or gas mixtures in the respective chamber, since the thermal conductivity of a given gas changes as a function of pressure. Depending on the type of gas atmosphere to be examined, the measuring method operating with detection of the radiation intensity may also be varied in such a manner that the analysis is based on the cooling process and thus the decreasing radiation emission of the previously heated surface as a function of time. While in the above-described methods, heating cycle and measuring cycle take place in synchronism, in an analysis by way of the decreasing radiation emission, heating cycle and measuring cycle must be successive.

As already discussed above in connection with the embodiment of a reactive system of gas/air, the respective curve of the radiation intensity or of the heating current is compiled by exothermal or endothermal reactions between individual gases of a mixed gas atmosphere. This can be catalytically accelerated with the appropriate design of the heatable surface. Absorption processes and desorption processes in each case lead to corresponding changes in the time curve of the detected radiation intensity and the detected heating current, respectively.

The method permits various variations. For example, the heatable surface may be catalytically active or inactive, absorbent or non-absorbent. As already discussed above, the heating rate may be varied. If the heating rate is raised quickly, possibly also with catalytically active surfaces, even reactive gas mixtures can be analyzed only by detecting their thermal conductivity. If the heating rate is increased slowly, the catalytic reaction is covered in addition to the conductivity. By appropriately selecting the heatable surface and with a corresponding energy supply, the surface temperature may be raised to the point that the cracking temperature of corresponding gas mixtures is reached. The chemical processes taking place when the cracking temperature is reached also lead to a detectable influence on the radiation intensity and/or the intensity of the heating current.

With the given electronic technology, the measurement signals may also be evaluated by way of microprocessors so that then a plurality of data can also be compiled by a small device, making it possible to manufacture handy devices of the size of a package of cigarettes also as low current consumption multi-function devices. The above further indicates that the method can be employed not only for the analysis of gases and gas mixtures but also for the analysis of mixtures of vapors and vapors with gases and gas mixtures.

Modifications will also be described in detail below with respect to their structure and mode of operation.

Figure 9:
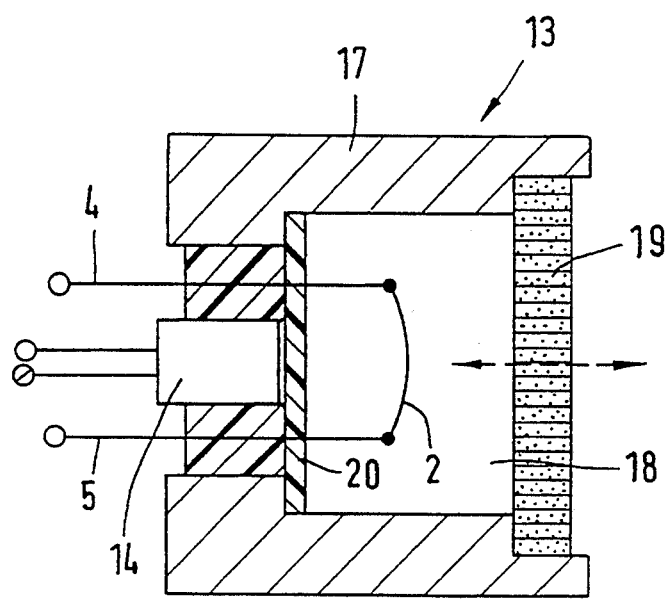
FIG. 9 depicts the structural configuration of a measuring cell for an arrangement according to FIG. 6.

FIG. 9 depicts a structural configuration of a measuring cell 13. This configuration is enclosed by a housing 17 enclosing a measuring chamber 18 intended to accommodate the measuring gas. At one side, the measuring chamber is provided with a gas passage 19 which, for example, in the form of a plate of porous sintered metal, serves as convection and flame barrier. The gas exchange here takes place by way of diffusion. An electrically heatable surface 2, for example, in the form of a wire is disposed in the measuring chamber, with the measuring chamber being terminated, on the side facing away from the gas passage, by a plate 20 made of a material that is transmissive for infrared radiation. On the rear side of the IR transmissive plate 20, an IR radiation sensor 14 is disposed. The input lead 4 and the output lead 5 for heating wire 2 pass through plate 20 and are encased in the housing together with radiation sensor 14.

Figure 10:
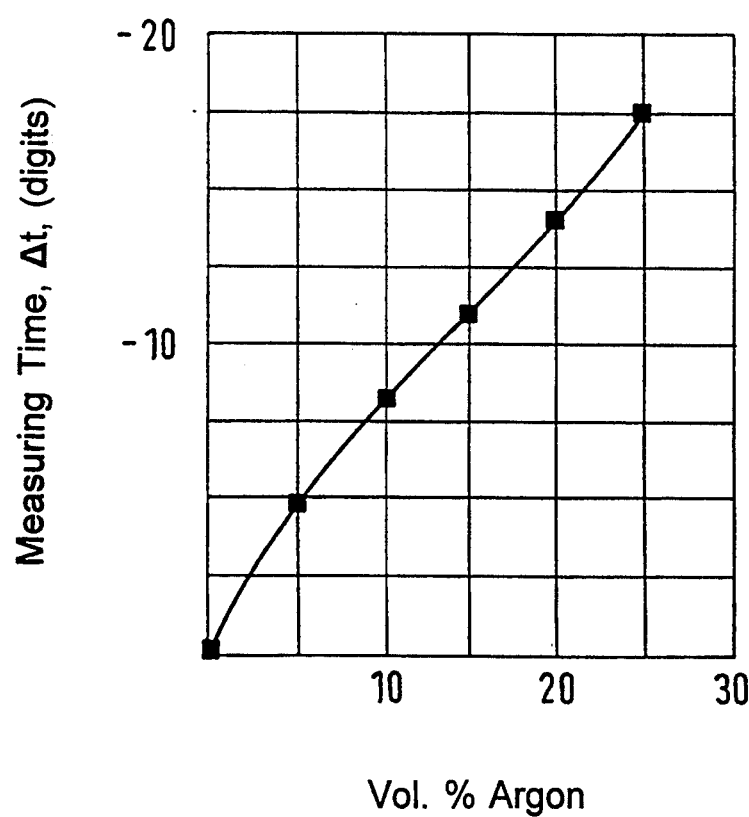
FIG. 10 is a measuring diagram for an argon-air mixture.

FIG. 10 depicts a calibration curve for argon-air mixtures recorded by a device according to FIG. 6. The electronic evaluation unit was here designed so that, after the calibration, the shift in the measuring time detected by a computer, as shown schematically in FIG. 8, was directly converted into volume percent. Compared to the measuring time for normal air, the reduction of the measuring period in which to detect an argon content of 25 volume percent was, for example, about 2 ms.

Figure 11:
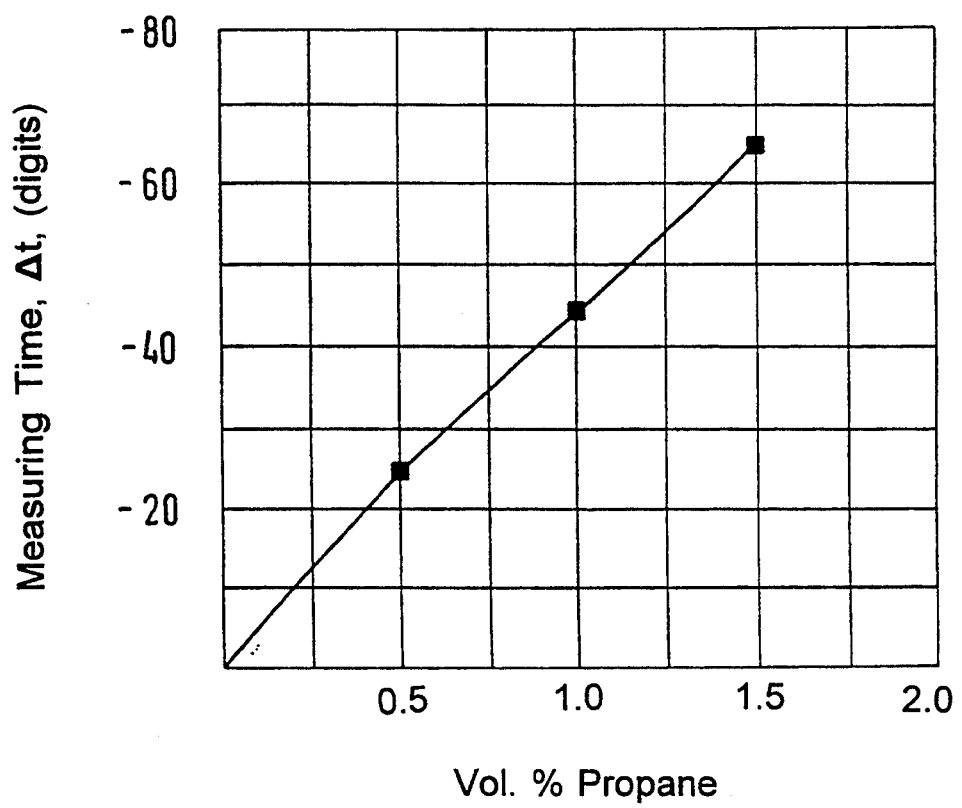
FIG. 11 is a measuring diagram for a propane-air mixture.

FIG. 11 depicts, as a comparison thereto, the measuring diagram recorded according to the same procedure for determining the propane content of air. The diagram depicts a sensitivity for the measuring process in the form of a shortening of the measuring period by about 4 ms per 1% propane (residual air).

Figure 12:
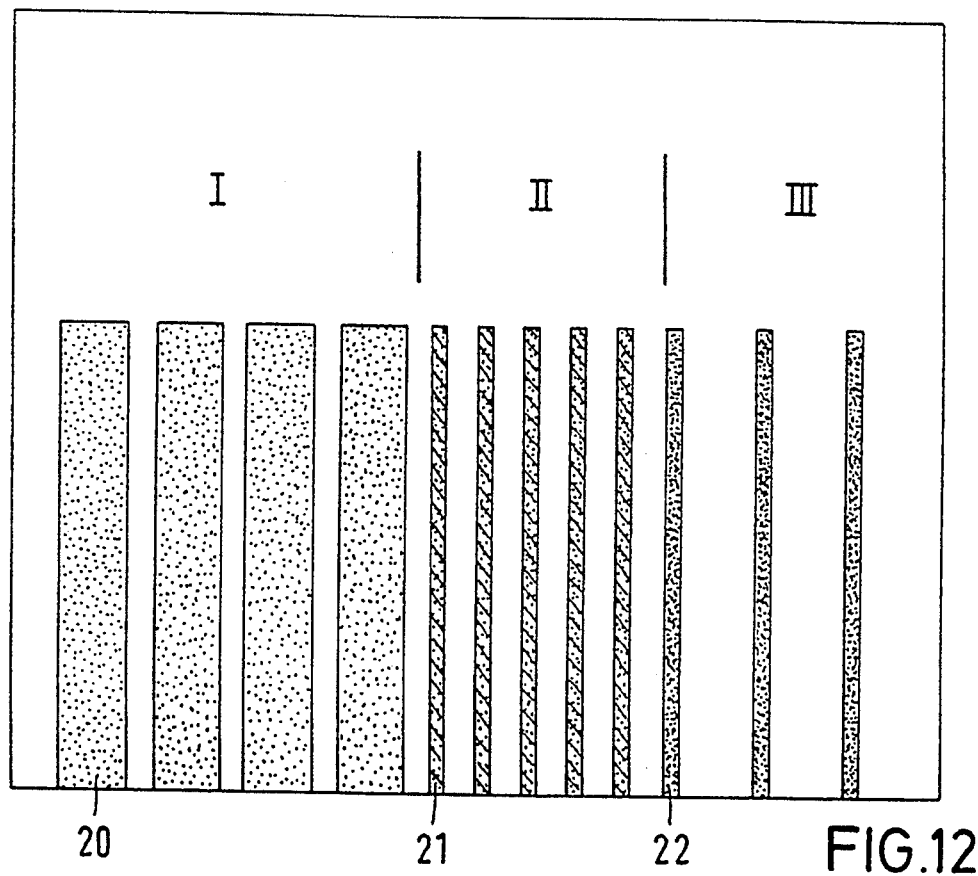
FIG. 12 is an oscillograph display of the method according to FIG. 6 for different gas-air mixtures.

FIG. 12 is a schematic representation, in the form of an oscillograph display, of a further mode of operation according to FIG. 6 for air (region I), for a methane-air mixture (region II) and for a hydrogen-air mixture (region III). The heating process is here clocked between a lower threshold and an upper threshold of radiation intensity. The dark bars 20 (for air), 21 (for air+methane) and 22 (for air+hydrogen) here represent the heating time. The spaces between the respective bars indicate the cooling periods. The device is set in such a way that, whenever the upper threshold is reached, the heating current is turned off and whenever the lower threshold is reached, the heating current is automatically turned on again so that the heating cycles are not fixedly given but set themselves freely as a function of the respective gas atmosphere to be measured.

If one now compares region I (air) with region II (air+methane), it is evident that, due to the onset of a thermal reaction, shorter heating times are required in a methane-air mixture to reach the upper threshold (radiation). However, it is characteristic that the cooling time between the individual cycles remains essentially unchanged. If one compares in this connection region III (air+hydrogen), it is again evident that, due to the thermal reaction between air and hydrogen, the heating period is shortened but that due to the afterglow effect in the air-hydrogen system, much longer cooling periods are required.

With the appropriate calibration, it thus becomes possible to detect the presence of different gases by way of a frequency measurement. Thus it is possible to perform selective measurements by detecting the heating and cooling periods.

Figure 13:
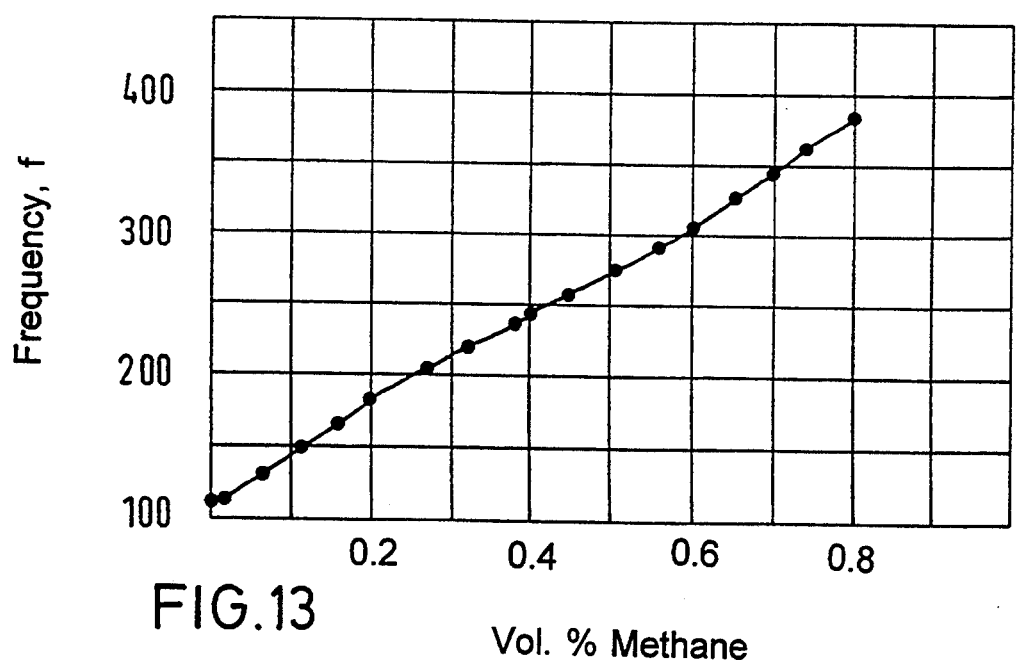
FIG. 13 is a frequency measuring diagram for a methane-air mixture, measured according to the method of FIG. 6 and FIG. 8.

FIG. 13 depicts in a measuring diagram the vibration behavior of a sensor of the type described in connection with FIG. 9 if two radiation intensity thresholds are provided analogously to the manner of operating described in connection with FIG. 12 as a function of the methane concentration in a methane-air mixture.

Figure 14:
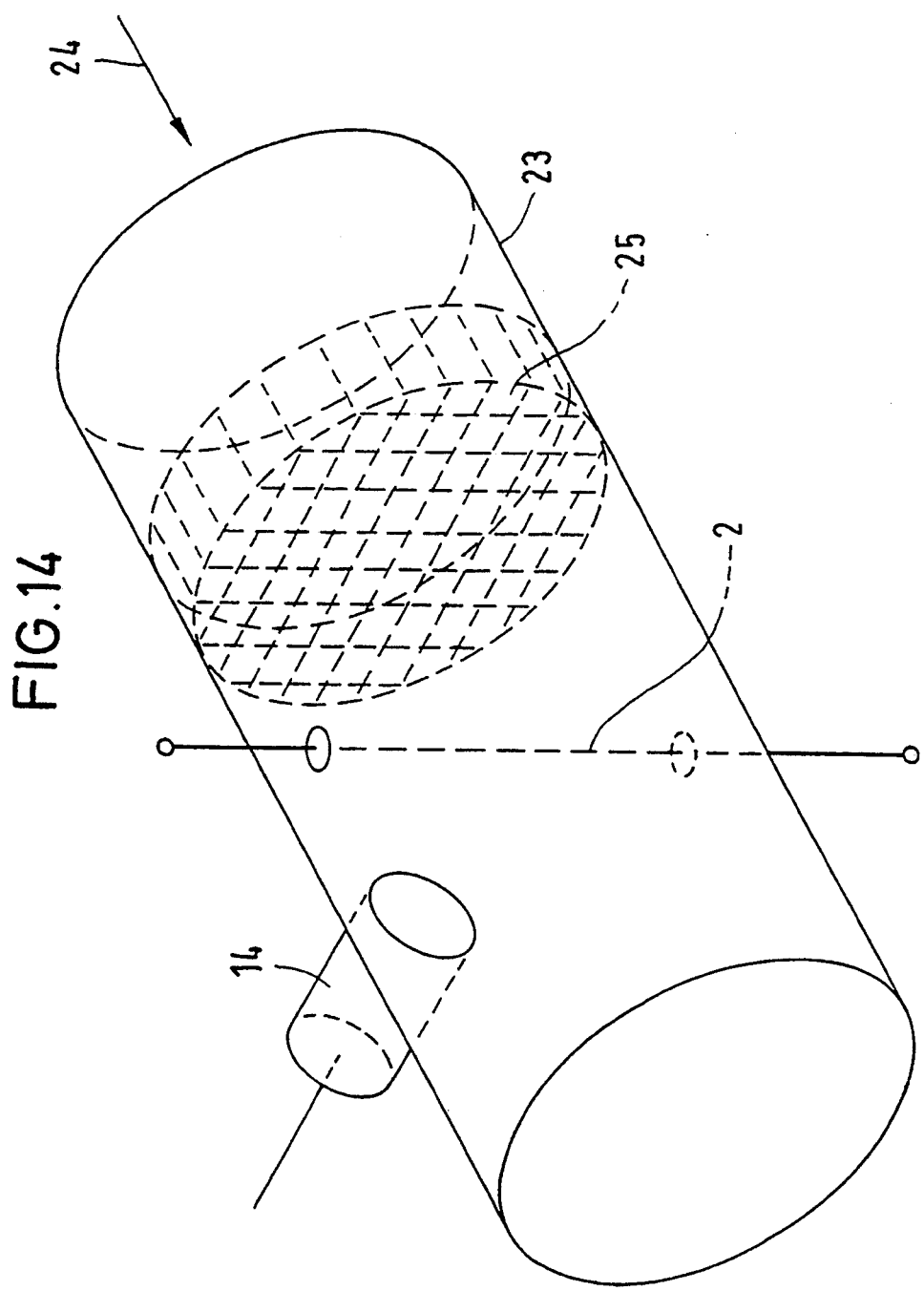
FIG. 14 depicts an embodiment for use of the method for measuring gas flow.

FIG. 14 is a perspective view of the measuring principle in its use as a flow meter, be it for a determination of gas flow in general, be it for a determination of gas velocity. For this purpose, a so-called flow rectifier 25 of conventional construction is disposed in a tube 23 through which the gas flows in the direction of the arrow 24. At an appropriate distance downstream of flow rectifier 25 there is again disposed an electrically heatable surface 2 in the form of a wire which diametrally passes through tube 23. A radiation sensor 14 by means of which changes can be detected in the heat discharge of wire 2 as a function of flow over time is disposed in the tube wall. Here again advantage is taken of the fact that the wire 2 need not be charged constantly with heating current but that the measuring process can be implemented at given time intervals.

Figure 15:
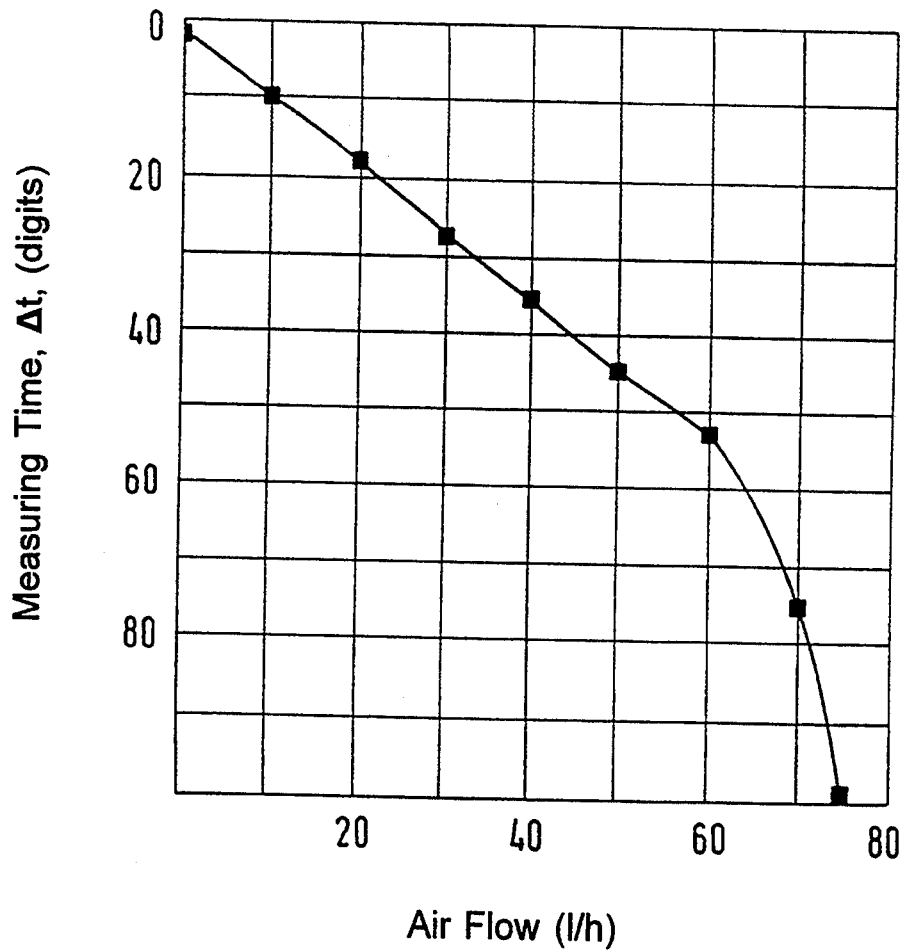
FIG. 15 is a flow measurement diagram.

FIG. 15 is a diagram of a measurement with which a changing flow through a tube was detected in the manner discussed above.

Figure 16:
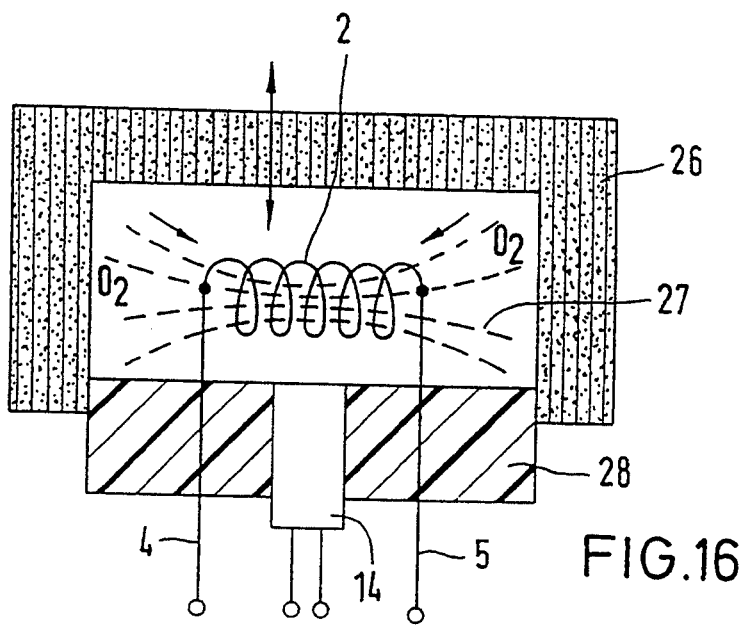
FIG. 16 depicts an embodiment for use of the method to determine the oxygen content of a gas mixture.

FIG. 16 depicts a modification of the measuring arrangement disclosed in connection with FIG. 9. In this embodiment, a heatable surface 2 in the form of a heating wire is disposed in a housing 26 that is essentially again formed of a porous material and serves as a convection barrier. Now, the heating wire lies in an inhomogeneous magnetic field that can be generated by coils through which currents flow, permanent magnets or the like. However, in the illustrated embodiment, the heating wire is configured as a helix so that it simultaneously forms a coil through which a corresponding magnetic field is built up if the coil is charged with the heating current. This is indicated by field lines 27. On the basis of the paramagnetic properties of oxygen, this arrangement permits an analysis of gaseous oxygen in gas mixtures in that, due to the magnetic wind creating convection of the oxygen in the region of heating wire 2, a change in the heat discharge of the heated surface can again be detected by way of IR sensor 14 which is associated with the heating coil in the illustrated manner and is installed in a gas impermeable fixed plate 28 of housing 26.

Figure 17:
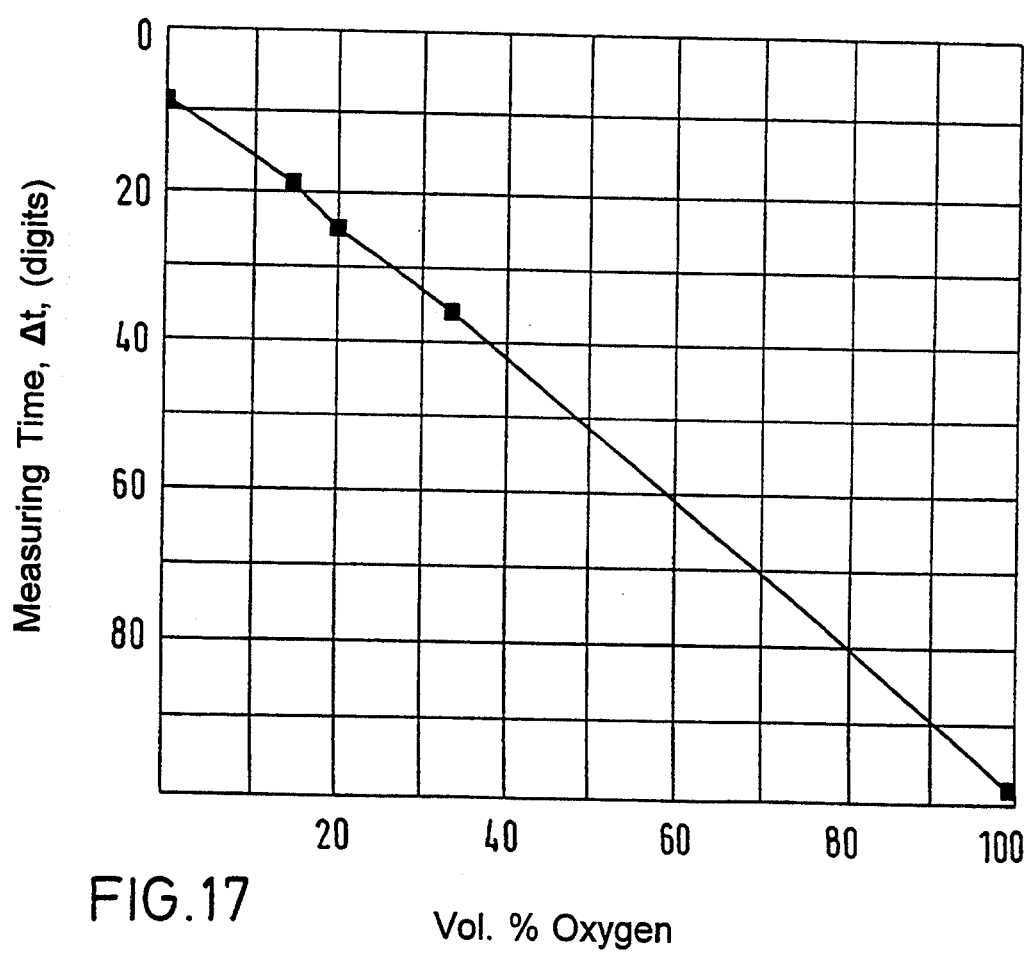
FIG. 17 is a measuring diagram of a determination of the oxygen content.

FIG. 17 displays, in a measuring diagram obtained from a measuring cell according to FIG. 16, the measurement values from different oxygen-nitrogen mixtures.

Figure 18:
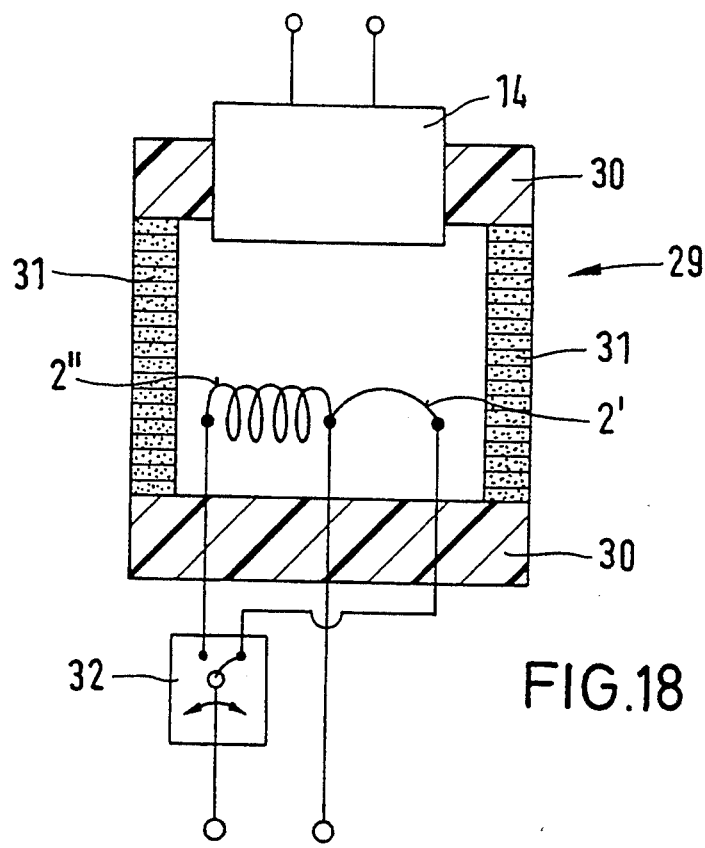
FIG. 18 depicts a combined arrangement for determining combustible components and the oxygen percentage in a gas atmosphere.

FIG. 18 depicts a measuring cell 29 which is a combination of the measuring cell 13 shown in FIG. 9 and the measuring cell 26 shown in FIG. 16. With the aid of such a measuring cell it is possible to analyze the combustible components and the oxygen content of gas mixtures. As indicated by the illustration, a smooth heating wire 2' and a heating wire 2" in the form of a coil are disposed in a housing 30 which is again terminated by plates 31 of a gas permeable material. Both heating wires are connected to a current supply. A radiation sensor 14 is again associated with the two heatable surfaces 2' and 2". By way of a switch 32, it is then possible to successively measure the oxygen content of the gas mixture and the combustible component in the above-described manner.

Figure 19:
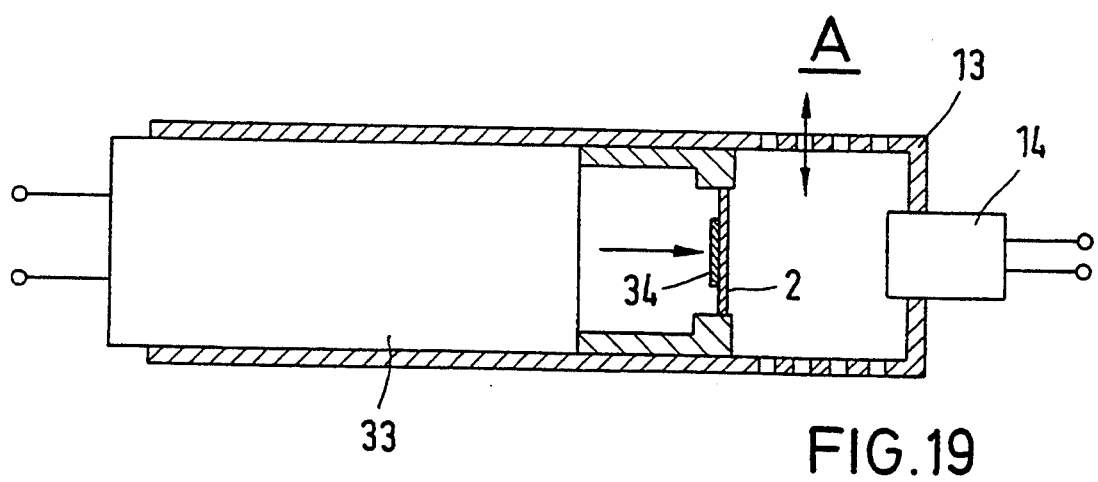
FIG. 19 depicts an embodiment for determining the moisture in gases by means of a sorption active heatable surface.

FIG. 19 depicts a further embodiment of a measuring cell. In this embodiment, measuring gas A is again able to enter into a measuring cell 13 through respective passages. Measuring cell 13 again includes a radiation sensor 14 which has an associated heatable surface. In this embodiment, the heatable surface 2 is configured to be sorption active, for example, in that it has a coating of aluminum oxide or silicon oxide on the side that is in contact with the measuring gas for moisture determination. The heatable surface in the form of a plate is heated from the rear by a laser 33 as an indirect, pulsating heat source. The heating spot on the rear of heatable surface 2 is provided with a thin plate 34 of platinum in order to prevent the surface from burning through. With such a measuring cell it is possible to determine the moisture in gases by way of the sorption behavior of water molecules on the heatable surface. With the appropriate configuration of the surface, other sorption processes can also be detected.

Figure 20:
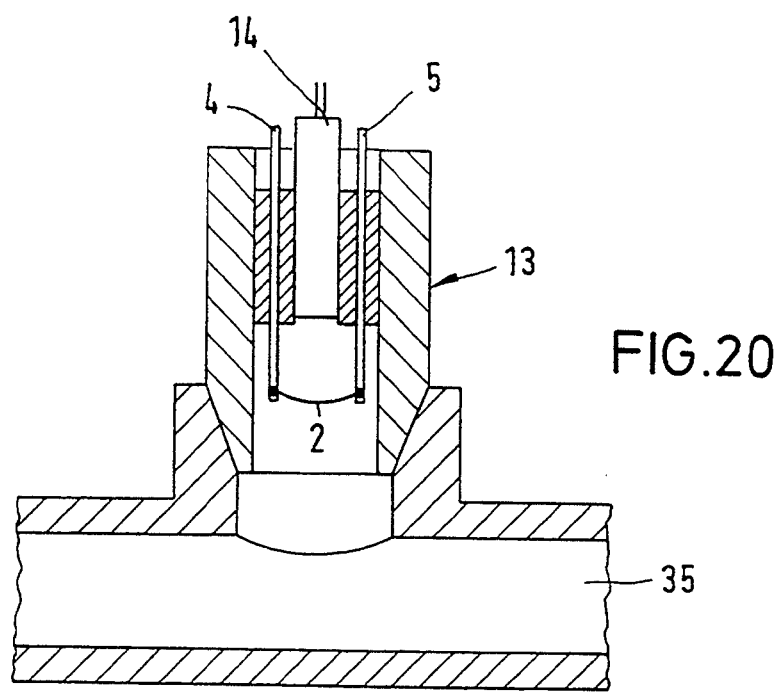
FIG. 20 depicts an embodiment for vacuum (pressure) determination.

FIG. 20 depicts the use for a pressure determination in a vacuum. For this purpose, a measuring cell 13 is provided in the circuit arrangement described in connection with FIG. 6. The heatable surface 2 of this measuring cell projects into chamber 35 in which the pressure is to be determined. The heatable surface 2 in the form of a wire has an associated radiation sensor 14, for example an IR sensor. Measuring cell 13 is here attached in a vacuum tight manner. Here again, the pressure determination is effected by detecting the heat transport of the gas molecules which becomes dominating beginning with a certain vacuum pressure by an increase in the free path length and thus produces detectable measuring results.

Figure 21:
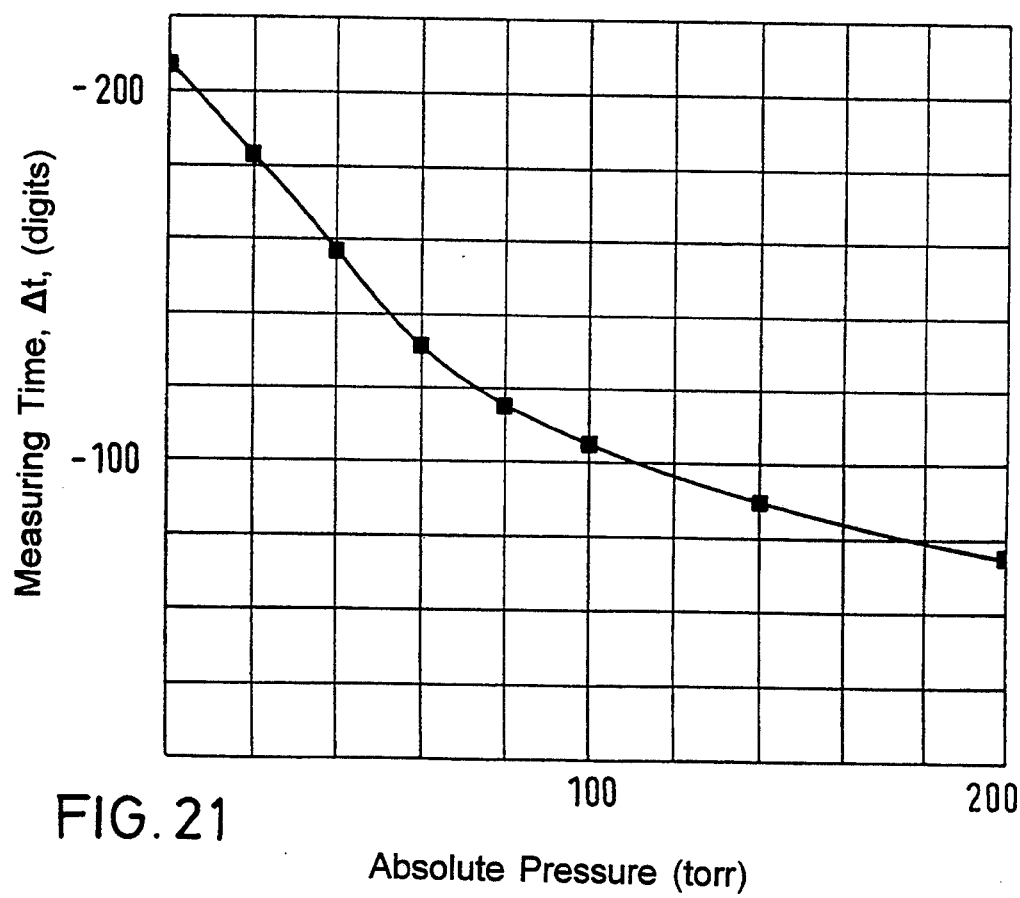
FIG. 21 is a pressure measurement diagram.

FIG. 21 depicts a measuring result in a range from 0 to 200 tort.

Figure 22:
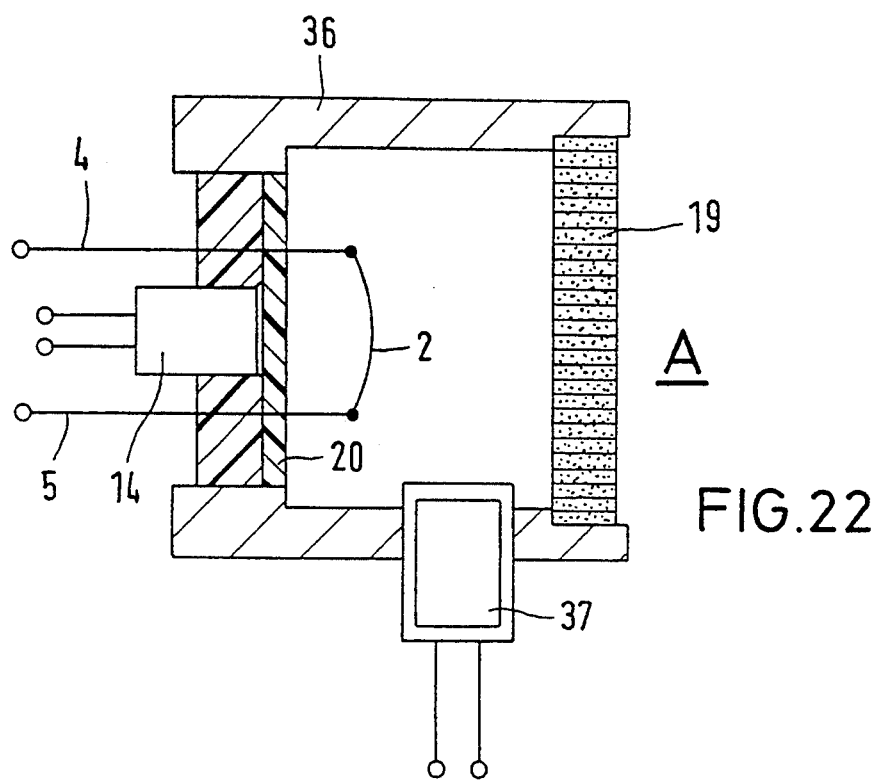
FIG. 22 depicts an embodiment for gas analysis by way of cracking at the heatable surface.

FIG. 22 depicts an embodiment of a measuring cell 36 with the aid of which it is possible, by way of a controlled thermal decomposition of gases with subsequently connected detection of the decomposition products, to make conclusions as to the concentration of the undecomposed gas. The measuring cell is again composed of a closed housing 36 including a gas permeable plate 19 so that the measuring gas A is able to enter into this closed chamber. A heatable surface in the form of a wire is disposed within the chamber and, as described in connection with FIG. 9, is in communication with a current supply and has an associated IR sensor 14 that is shielded by a plate 20 of an IR transmitting material. Additionally, a gas sensor 37, for example, a semiconductor or an electro-chemical sensor projects into the interior; this sensor is designed for the determination of a certain gas as the decomposition product.

If now, for example, it is to be determined whether the measuring gas contains a chlorofluorocarbon, for example CFC(R12), the heatable surface 2 is heated to such an extent that the cracking temperature of the CFC is reached, possibly after catalytic reduction. If CFC is contained in the measuring gas, the cracking splits off the chlorine. Gas sensor 37 is here designed to detect chlorine so that the presence of CFC can be detected by way of the released chlorine.

Figure 23:
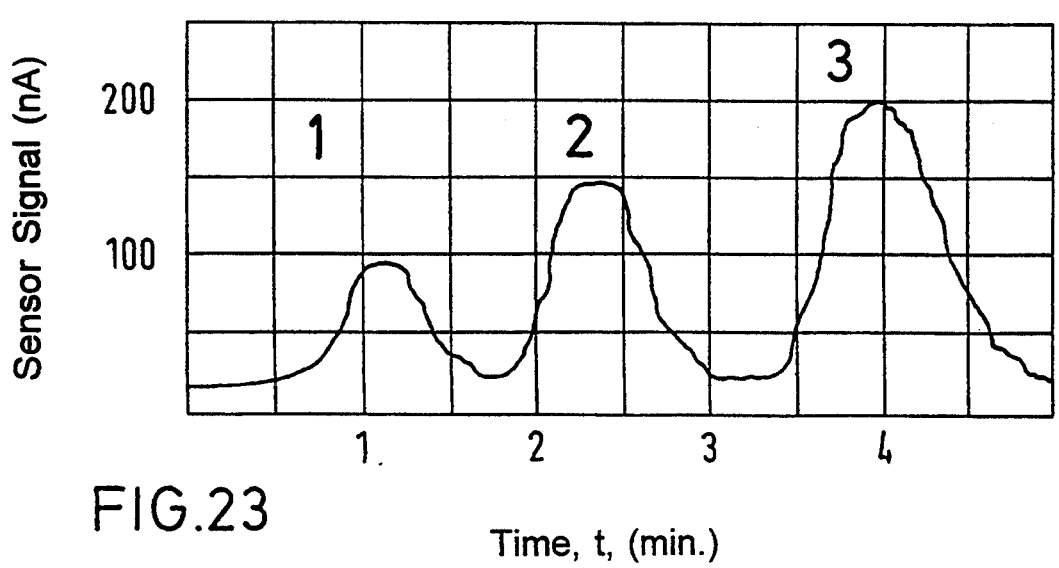
FIG. 23 is a measurement diagram for analyzing a chlorofluorocarbon.

FIG. 23 depicts a measuring diagram. With a composition of the measuring gas of 0.5% R12 in air, the glow wire was heated three times in succession at intervals of about two minutes. During the first measurement, the cracking temperature was maintained for two seconds, during the second measurement for four seconds and during the third measurement for eight seconds. As indicated by the measuring diagram, the chlorine sensor was able to detect the presence of chlorine at each measuring point, with the detected quantity of chlorine being approximately proportional to the decomposition time. Thus it has been demonstrated that, according to the method of the invention, reliable and repeatable measuring results can be obtained for this individual case as well.

Figure 24:
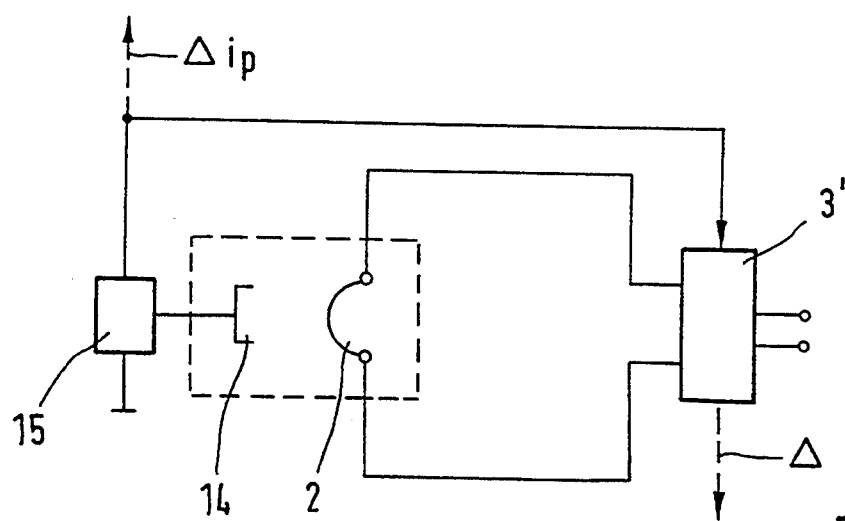
FIG. 24 is a block circuit diagram of a continuous monitoring device.

FIG. 24 is a block circuit diagram of an embodiment that has been simplified compared to FIG. 6 and as it is advisable, in particular, for stationary gas warning devices having an external current supply. Measuring cell 13 again includes a heatable surface 2 in the form of a heating wire through which current flows and in which a predetermined current I flows constantly with a predetermined voltage V. By way of the set value generator 15, a radiation intensity threshold is set which is characteristic for the noxious gas to be expected in the atmosphere being monitored. If now the noxious gas flows in, the radiation intensity that is continuously detected by radiation sensor 14 changes; for example it rises up to a given threshold. Thus, the set value generator initiates a signal which takes back the heating current by way of a regulating device in electrical energy supply 3' and at the same time initiates an alarm and/or control signal (alarm output A). At the same time, the heating wire is protected against undue overheating. However, the alarm signal may also be initiated directly by way of set value generator 15, as indicated by signal path $\Delta i_p$.

The heating current may now either be switched off entirely or reduced only until the predetermined lower intensity threshold is reached again. Thus the sensitivity of the system is reduced. Instead of changing or reducing the heating current, the heating voltage may also be changed correspondingly.

What is claimed is:

1. A method of determining at least one of chemical properties, physical properties and physical states of a gas atmosphere, comprising the steps of:
   a. bringing the gas atmosphere into contact with a heatable surface while heating up the heatable surface from a starting temperature to a predetermined higher temperature by the addition of energy thereto over a period of heating time;
   b. discontinuing the addition of energy when the predetermined higher temperature is reached; and
   c. evaluating heat discharged by the heatable surface under the influence of the gas atmosphere as a function of time to generate a measuring signal.

2. The method according to claim 1, wherein heating up of the heatable surface by the addition of energy is effected over a period of heating time which is a limited period of heating time, and occurs cyclically at successive intervals in time as a heating cycle.

3. The method according to claim 2, wherein, after the addition of energy is discontinued in one period of heating time, the heatable surface is reheated again whenever a predetermined minimum temperature is reached.

4. The method according to claim 2, wherein the successive intervals in time between each period of heating time are fixed.

5. The method according to claim 2, wherein the period of heating time has a beginning determined by a given lower measuring value threshold and an end determined by a given upper measuring value threshold, and wherein the succession in time of the period of heating serves as the measuring signal for analyzing the gas atmosphere.

6. The method according to claim 2, wherein the heat discharged by the heatable surface is evaluated by measuring radiation intensity of thermal radiation emanating from the heatable surface.

7. The method according to claim 6, wherein the heating cycle begins with heating up of the heatable surface in step (a), and wherein time is measured during which, starting at the beginning of the heating cycle, the radiation intensity reaches a predetermined radiation intensity threshold.

8. The method according to claim 2, wherein the energy added to heat up the heatable surface is electrical energy, and wherein the heat discharged by the heatable surface under the influence of the gas atmosphere is evaluated by measuring electrical current required to heat the heatable surface at a predetermined voltage.

9. The method according to claim 2, wherein the measuring signal is an electrical signal.

10. The method according to claim 1, wherein the heat discharged by the heatable surface is evaluated by measuring radiation intensity of thermal radiation emanating from the heatable surface.

11. The method according to claim 10, wherein the heating cycle begins with heating up of the heatable surface in step (a), and wherein time is measured during which, starting at the beginning of the heating cycle, the radiation intensity reaches a predetermined radiation intensity threshold.

12. The method according to claim 1, wherein the energy added to heat up the heatable surface is electrical energy, and wherein the heat discharged by the heatable surface under the influence of the gas atmosphere is evaluated by measuring electrical current required to heat the heatable surface at a predetermined voltage.

13. The method according to claim 1, wherein the measuring signal is an electrical signal.

* * * * *